United States Patent
Lima et al.

(10) Patent No.: US 11,028,835 B2
(45) Date of Patent: Jun. 8, 2021

(54) ARTIFICIAL MUSCLE ACTUATORS

(71) Applicant: Lintec of America, Inc., Richardson, TX (US)

(72) Inventors: Marcio Dias Lima, Richardson, TX (US); Yang Yang, Richardson, TX (US); Luis Plata, Richardson, TX (US); Marilu Guerrero, Richardson, TX (US); Franklin Le, Richardson, TX (US); Randy Allen, Richardson, TX (US)

(73) Assignee: LINTEC OF AMERICA, INC., Richardson, TX (US)

( * ) Notice: Subject to any disclaimer, the term of this patent is extended or adjusted under 35 U.S.C. 154(b) by 0 days.

(21) Appl. No.: 16/466,532

(22) PCT Filed: Dec. 7, 2017

(86) PCT No.: PCT/US2017/065150
§ 371 (c)(1),
(2) Date: Jun. 4, 2019

(87) PCT Pub. No.: WO2018/106940
PCT Pub. Date: Jun. 14, 2018

(65) Prior Publication Data
US 2019/0277266 A1    Sep. 12, 2019

Related U.S. Application Data

(60) Provisional application No. 62/462,544, filed on Feb. 23, 2017, provisional application No. 62/431,717, filed on Dec. 8, 2016.

(51) Int. Cl.
*F03G 7/06*    (2006.01)
*F16K 31/44*    (2006.01)
(Continued)

(52) U.S. Cl.
CPC ............... *F03G 7/06* (2013.01); *F16K 31/44* (2013.01); *H01H 85/04* (2013.01);
(Continued)

(58) Field of Classification Search
CPC ......... F03G 7/06; H02N 11/006; F16K 31/44; H01B 1/18
See application file for complete search history.

(56) References Cited

U.S. PATENT DOCUMENTS

| 3,810,062 A | 5/1974 | Kozacka |
| 3,969,695 A | 7/1976 | Belcher |

(Continued)

FOREIGN PATENT DOCUMENTS

| DE | 10 2006 029 693 A1 | 3/2007 |
| EP | 1 693 950 A1 | 8/2006 |

(Continued)

OTHER PUBLICATIONS

English Translation JP 2007159222A (Year: 2007).*

(Continued)

*Primary Examiner* — Shafiq Mian
(74) *Attorney, Agent, or Firm* — Greenblum & Bernstein, P.L.C.

(57) ABSTRACT

A hinge-type actuator device in accordance with the present disclosure may include a first and second paddle, a first and second artificial muscle actuator segment, and a plurality of contacts, where the first and second artificial muscle actuator segments are actuated via the contacts, actuation of the first artificial muscle actuator segment causes the first and second paddle to open the hinge-type actuator, and actuation of the second artificial muscle actuator segment causes the first and second paddle to close the hinge-type actuator.

3 Claims, 7 Drawing Sheets

(51) Int. Cl.
*H02N 11/00* (2006.01)
*H01H 85/04* (2006.01)
*H01B 1/18* (2006.01)
*A61F 2/50* (2006.01)

(52) U.S. Cl.
CPC .... *H02N 11/006* (2013.01); *A61F 2002/5066* (2013.01); *F03G 7/065* (2013.01); *H01B 1/18* (2013.01)

(56) References Cited

U.S. PATENT DOCUMENTS

| | | | |
|---|---|---|---|
| 5,229,739 A | 7/1993 | Oh et al. | |
| 5,963,121 A | 10/1999 | Stygar et al. | |
| 7,117,673 B2* | 10/2006 | Szilagyi | B23Q 1/5462 60/528 |
| 7,256,518 B2* | 8/2007 | Gummin | F03G 7/065 310/12.33 |
| 7,692,361 B2 | 4/2010 | Kato | |
| 8,633,795 B2 | 1/2014 | Knab et al. | |
| 9,425,010 B2 | 8/2016 | Hentschel | |
| 2002/0113684 A1* | 8/2002 | Arikawa | H01H 85/185 337/163 |
| 2004/0104801 A1 | 6/2004 | Jollenbeck et al. | |
| 2005/0160858 A1* | 7/2005 | Mernoe | G05G 19/00 74/469 |
| 2006/0125596 A1 | 6/2006 | Darr et al. | |
| 2006/0261709 A1 | 11/2006 | Kato et al. | |
| 2007/0132539 A1 | 6/2007 | Richter et al. | |
| 2007/0193267 A1* | 8/2007 | He | F03G 7/065 60/527 |
| 2010/0060406 A1 | 3/2010 | Kim et al. | |
| 2010/0234779 A1 | 9/2010 | Asvadi et al. | |
| 2011/0279218 A1 | 11/2011 | Salonga et al. | |
| 2014/0132119 A1 | 5/2014 | Whinnery et al. | |
| 2014/0163664 A1 | 6/2014 | Goldsmith | |
| 2015/0219078 A1* | 8/2015 | Li | H02N 10/00 310/306 |

FOREIGN PATENT DOCUMENTS

| | | |
|---|---|---|
| JP | 56-130054 A | 10/1981 |
| JP | 60-77264 U | 5/1985 |
| JP | 11-215793 A | 8/1999 |
| JP | 2005-110494 A | 4/2005 |
| JP | 2005-176428 A | 6/2005 |
| JP | 2006-325335 A | 11/2006 |
| JP | 2007159222 A | 6/2007 |
| JP | 2007159222 A * | 6/2007 |
| JP | 2007-300714 A | 11/2007 |
| JP | 2008-100901 A | 5/2008 |
| JP | 2009-32773 A | 2/2009 |
| JP | 2010-500895 A | 1/2010 |
| JP | 2011-125092 A | 6/2011 |
| JP | 2011-152031 A | 8/2011 |
| JP | 2012-530572 A | 12/2012 |
| JP | 2016-199900 A | 12/2016 |
| KR | 101 563 105 B1 | 10/2015 |
| KR | 20160117658 A | 10/2016 |
| WO | 2005/027333 A1 | 3/2005 |
| WO | 2011/070912 A1 | 6/2011 |

OTHER PUBLICATIONS

Office Action issued in corresponding U.S. Appl. No. 16/467,830 dated May 8, 2020 (13 pages).
Japan Official Action (Notice of Reasons for Rejection) issued in JP 2019-522498, dated Aug. 11, 2020, and English language translation thereof.
U.S. Appl. No. 16/466,131 to Marcio Dias Lima et al., filed Jun. 3, 2019.
U.S. Appl. No. 16/467,830 to Marcio Dias Lima et al., filed Jun. 7, 2019.
Taiwanese Official Letter issued in Corresponding Taiwanese Patent Application No. 106143209 dated Feb. 10, 2020 (4 pages).
International Search Report issued in PCT/US2017/065127 dated May 14, 2018 (5 pages).
Written Opinion issued in PCT/US2017/065127 dated May 14, 2018 (9 pages).
International Search Report issued in PCT/US2017/065151 dated May 14, 2018 (6 pages).
Written Opinion issued in PCT/US2017/065151 dated May 14, 2018 (8 pages).
ACESElectromaterials: "Artificial muscles"; XP054978158; Aug. 4, 2015 (Aug. 4, 2015); retrieved from YouTube [online]: URL:https://www.youtube.com/watch?v=vVhUBENOqhg Time frame: 1:21-1:37.
International Preliminary Report on Patentability issued in Application No. PCT/US2017/065150, dated Jun. 20, 2019 (11 pages).
International Preliminary Report on Patentability issued in Application No. PCT/US2017/065127, dated Jun. 20, 2019 (10 pages).
International Preliminary Report on Patentability issued in Application No. PCT/US2017/065151, dated Jun. 20, 2019 (9 pages).
International Search Report issued in International Application No. PCT/US2017/065150 dated May 14, 2018 (5 pages).
Written Opinion issued in International Application No. PCT/US2017/065150 dated May 14, 2018 (10 pages).
Japan Notice of Reasons for Rejection in JP Appl. No. 2019-530463, dated Sep. 7, 2020 and English translation.
Japan Notice of Reasons for Rejection in JP Appl. No. 2019-524041, dated Sep. 7, 2020 and English translation.
Japanese Official Action received in JP Application No. 2019-524041, dated Mar. 1, 2021 and English language translation thereof.

* cited by examiner

ARTIFICIAL MUSCLE ACTUATORS

CROSS-REFERENCE TO RELATED APPLICATIONS

This application claims priority, pursuant to 35 U.S.C. § 119(e) to U.S. Provisional Application 62/431,717 filed on Dec. 8, 2016, and U.S. Provisional Application 62/462,544 filed on Feb. 23, 2017, and which are incorporated by reference in their entireties.

BACKGROUND OF INVENTION

Thermally driven torsional actuators based on twisted polymeric and carbon nanotube (CNT) fibers and yarns have a wide range of applications. Artificial muscle actuators comprising twisted and/or coiled polymers have the advantage of low cost, high production volume, and design simplicity. Artificial muscle actuators may have advantages over small motors because of the greatly simplified engineering and lower product costs.

SUMMARY

In one aspect, a hinge-type actuator device in accordance with the present disclosure may include a first and second paddle, a first and second artificial muscle actuator segment, and a plurality of contacts, wherein the first and second artificial muscle actuator segments are actuated via the contacts, actuation of the first artificial muscle actuator segment causes the first and second paddle to open the hinge-type actuator, and actuation of the second artificial muscle actuator segment causes the first and second paddle to close the hinge-type actuator.

In another aspect, a linear displacement device in accordance with the present disclosure may include at least one artificial muscle actuator, an arm attached to the at least one artificial muscle, a body that is restricted to move along a line, and a stationary channel that restricts the motion of the body to linear motion, wherein the at least one artificial muscle actuator causes the body to move along the line, wherein the body is further restricted to move along a surface of the arm, wherein the at least one artificial muscle actuator is a rotational muscle actuator, and wherein the arm rotates in concert with the at least one artificial muscle actuator.

In another aspect, a linear displacement device in accordance with the present disclosure may include at least one artificial muscle actuator, and a body that is restricted to move along a line, wherein the at least one artificial muscle actuator causes the body to move along the line, wherein one of the at least one artificial muscle actuators expands when actuated, wherein one of the at least one artificial muscle actuators contracts when actuated, and wherein a first end of each of the artificial muscle actuators is attached to a base and a second end of each of the artificial muscle actuators is attached to the body.

In another aspect, a mechanical accumulator in accordance with the present disclosure may include at least one rotational artificial muscle, an arm attached to the at least one artificial muscle, and a latching mechanism that maintains an initial position of the mechanical unless a predetermined amount of force is applied by the at least one rotational artificial muscle, wherein the arm rotates in concert with the at least one rotational artificial muscle actuator.

Other aspects and advantages of the claimed subject matter will be apparent from the following description and the appended claims.

BRIEF DESCRIPTION OF DRAWINGS

Certain embodiments of the disclosure will hereafter be described with reference to the accompanying drawings, where like reference numerals denote like elements. It should be understood, however, that the accompanying figures illustrate the various implementations described herein and are not meant to limit the scope of various technologies described herein.

FIG. 5 has plan and side views.

DETAILED DESCRIPTION

Figure 1:
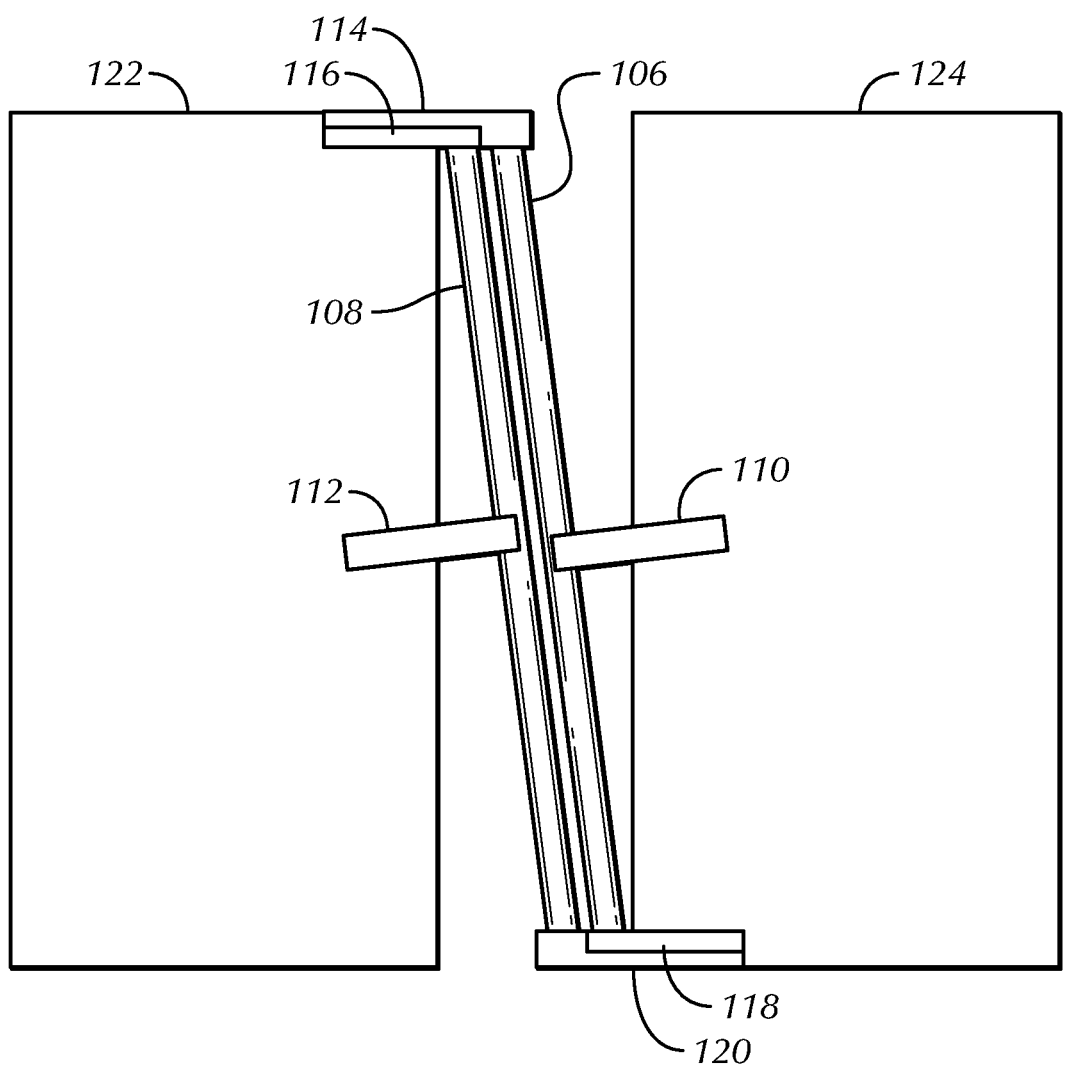
FIG. 1 is a schematic of a hinge-type actuator in accordance with one or more embodiments disclosed herein.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Embodiments of the present disclosure will now be described in detail with reference to the accompanying figures. Like elements in the various figures may be denoted by like reference numerals for consistency. Further, it will be apparent to one of ordinary skill in the art that the embodiments disclosed herein may be practiced without the specific details provided to allow a more thorough understanding of the claimed subject matter. Further still, one of ordinary skill in the art will readily recognize that the scale of the elements in the accompanying figures may vary without departing from the scope of the present disclosure.

The term "or" is understood to be an "inclusive or" unless explicitly stated otherwise. Under the definition of "inclusive or," the expression "A or B" is understood to mean "A alone, B alone, or both A and B." Similarly, "A, B, or C" is understood to mean "A alone, B alone, C alone, both A and B, both A and C, both B and C, or A and B and C."

The artificial muscle actuators may be comprised of any type of artificial muscle. Artificial muscle materials may include polymers, carbon nanotubes (CNTs), or any other suitable material. In one or more embodiments, a nylon fiber may be twisted into a coiled shape with small copper wire wound around the nylon to provide electrical conductivity. Nylon is relatively abundant and inexpensive. Other materials may be desired for their greater actuation speeds, temperatures, durability, precision, or other useful property.

In accordance with embodiments disclosed herein, a carbon nanotube actuator comprised of a plurality of carbon nanotube (CNT) sheets stacked on top of each other may be used. In one or more embodiments, the plurality of CNT sheets may comprise a single sheet wrapped over on itself multiple times. Such CNT sheets may be considered isotropic in accordance with embodiments disclosed herein. In one or more embodiments, these CNT sheets, when stacked on top of each other, become essentially inseparable and cannot be unwrapped. CNT layers in some cases may contain 50 CNT sheets, 100 CNT sheets, or more.

Muscle actuators may be activated with application of heat supplied by applying a voltage across the material. Other possibilities include chemical reaction based artificial muscle actuators and heat-activated muscle actuators heated through means other than an applied voltage. Other heating means include induction heating, magnetic hysteresis, the direct application of heat and the like. Still other possibilities are absorption-activated and photonically-activated artificial muscle actuators.

An artificial muscle may also be referred to as a sheet muscle, a hybrid nanofiber artificial muscle, a hybrid muscle, a hybrid actuator, an artificial muscle actuator, or the like.

The term hybrid is used to indicate that CNT sheets are infiltrated with a guest actuation material to form one or more CNT layers, and further that the CNT layers may include other materials as well. For example, materials may include elastomers (e.g., silicone-based rubber, polyurethane, styrene-butadiene copolymer, natural rubber, and the like), fluorinated plastics (e.g., perfluoroalkoxy alkane (PFA), polytetrafluoroethylene (PTFE), fluorinated ethylene propylene (FEP), and the like), aramids, (e.g., Kevlar, nomex, and the like), epoxies, polyimides, paraffin wax, and the like.

In embodiments disclosed herein, a yarn is a long, continuous length of one or more fibers. In a CNT yarn, the fibers are CNTs, and a core fiber may be the fiber around which CNT layers are wrapped.

In general, embodiments of the invention relate to advancements in muscle fiber actuator technologies. For example, one or more embodiments of the present disclosure relate to artificial muscle actuators. One or more embodiments include a hinge-type actuator. One or more embodiments include a linear displacement, or button-type, actuator. One or more embodiments include a mechanical accumulator, or catapult-type, actuator. One of ordinary skill in the art will appreciate that the embodiments disclosed herein may be used in combination with other embodiments, or incorporated into other existing actuator technologies, such as those incorporated by reference above.

Embodiments of the invention include actuator materials, or artificial muscles, including twist-spun nanofiber yarn and twisted polymer fibers that generate torsional and/or tensile actuation when powered electrically, photonically, thermally, chemically, by absorption, or by other means. Embodiments of the invention include actuators that utilize coiled yarns or polymer fibers and may be either neat or include a guest.

In one or more embodiments, an artificial muscle actuator may function as a hinge-type structure.

FIG. 1 is a schematic of a hinge-type actuator in accordance with one or more embodiments disclosed herein. In FIG. 1, two artificial muscle actuators 106, 108 are arranged parallel to each other and designed to rotationally actuate in opposite directions. FIG. 1 also includes electrical and/or physical contacts 110, 112, 114, 116, 118, 120 between the artificial muscle actuators 106, 108 and the paddles 122, 124. Thus, in one or more embodiments, electrical connections may serve as mechanical connections from the paddles to the artificial muscle actuators. In these embodiments, the artificial muscle actuators 106, 108 are not rigidly held in a diagonal position, but rather are flexible. Also, each artificial muscle actuator 106, 108 is connected to both paddles 122, 124, which is necessary to facilitate the desired motion. Further, when one of artificial muscle actuators 106, 108 is activated to close the hinge, the hinge may close without the artificial muscle actuators 106, 108 colliding with each other and hindering the motion.

In these embodiments, the contacts 110, 112, 114, 116, 118, 120 may be electrical, and addition physical contacts may be provided between the artificial muscle actuators 106, 108 and the paddles 122, 124. In this context, physical contacts physically connect the paddles to the artificial muscle actuators such that actuation moves the paddles. Electrical contacts enable current to be applied to the artificial muscle actuators for actuation.

For example, referring to FIG. 1, an electrical current may pass through the contact 110 through the artificial muscle actuator 106 to the other contacts 114, 118. The electrical current will heat up the artificial muscle actuator and activate it, causing the paddles 122, 124 to come together. Similarly, an electrical current supplied through the contact 112 to the contacts 116, 120 will cause actuation in the artificial muscle actuator 108, which in turn causes the paddles 122, 124 to separate. Each artificial muscle actuator 106, 108, may thus be operated independently of the other and may be operated as a bi-stable system.

In the embodiments of FIG. 1, the artificial muscle fibers 106, 108 are bound together on each paddle 122, 124. The connectors 114, 116 (and connectors 118, 120) may be electrically connected to each other and may serve as grounding connections, as well as physical connections between the artificial muscle fibers 106, 108 and paddles 122, 124.

Figure 2:
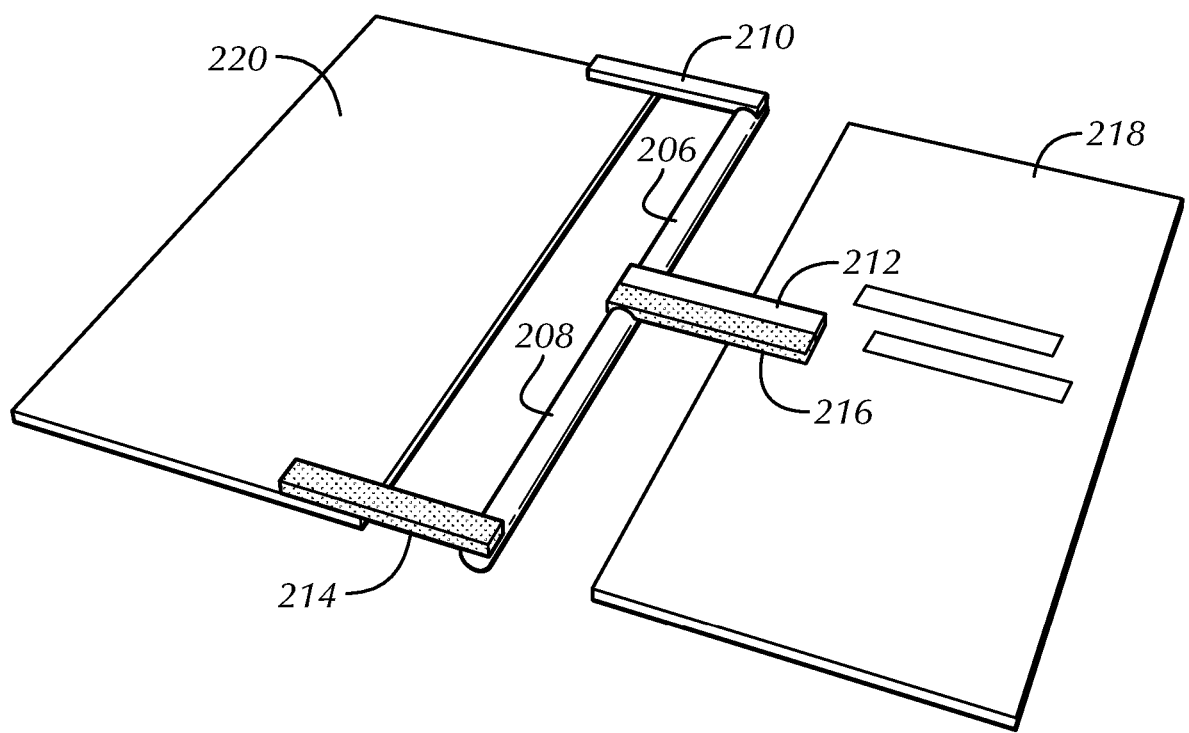
FIG. 2 is another schematic of a hinge-type actuator in accordance with one or more embodiments disclosed herein.

FIG. 2 is a schematic of another hinge-type actuator in accordance with one or more embodiments disclosed herein. The embodiments illustrated in FIG. 2 include two artificial muscle actuators 206, 208 linearly aligned and configured to actuate in opposite directions. FIG. 2 also includes electrical and/or physical contacts 210, 212, 214, 216 as in the embodiments described with reference to FIG. 1. The linear actuators 206, 208 may be constructed from a single artificial muscle fiber, with the electrical contacts defining the difference between the artificial muscle actuator 206 and the artificial muscle actuator 208. Two of the contacts 212, 216 are located at the junction of the two artificial muscle actuators 206, 208, while contacts 210, 214 are located at ends of each of the artificial muscle actuators 206, 208, respectively.

In these embodiments, an electrical current may pass through the contact 210 through the artificial muscle actuator 206 to the other contact 212. The electrical current will heat up the artificial muscle actuator 206 and activate it, causing the paddles 218, 220 to come together. Similarly, an electrical current supplied through the contact 214, 216 will cause actuation in the artificial muscle actuator 208, causing the paddles 218, 220 to separate.

The embodiments described in FIG. 2 may be more compact than those of FIG. 1. However, the embodiments of FIG. 1 may provide more torque during actuation. One of ordinary skill in the art will appreciate that the configuration may be selected or modified depending on the specific application.

The embodiments disclosed above and in FIGS. 1 and 2 may be used for any hinge-type actuation. For example, self-opening and closing hatches, doors, laptops, lids, books, origami, and the like. For example, a possible device may be a simple box that can be configured to automatically unfold and refold with the application of electric current. The configurations presented herein would be resistant to actuating with changes in ambient temperature because the two muscle actuators would oppose each other's movement.

Embodiments disclosed herein also include smooth reversal of actuation. For example, one or more embodiments of artificial muscle actuator device may be configured to rotate a paddle in an arc, reverse direction and then rotate in the opposite direction. In some applications, if sensitive devices are mounted onto the paddle, it may be desirable that a stop of the actuation and a reversal of direction be made as smoothly as possible. In these embodiments, the applied currents are decreased slowly for a few steps, stopped, and then ramped up in the reverse direction equally slowly. As such, for example, the actuation of a paddle with a mounted device may come to a smooth stop and reverse direction with no jerking behavior.

In one or more embodiments, an artificial muscle actuator may be a linear displacement, or button-type, device. In one or more embodiments, a linear displacement device may exhibit spring-like behavior, but yet can still be controlled electrically. The artificial muscle actuators suspending the linear displacement device are capable of providing the elastic ability similar to a spring, while still being controllable using electronics. If spring-like motion is not desired, then the linear displacement device may be configured to have one or more latching mechanisms, for example, mechanical or magnetic latches, that hold the linear displacement device in position. The latching mechanisms may be desired to prevent the linear displacement device from moving slightly. A predetermined amount of force may then be required to displace the linear displacement device from a latched position. The spring-like behavior of the artificial muscle actuators would return the linear displacement device to the stable latched position when the external force is removed. In one or more embodiments, there may be two or more stable positions for the artificial muscle actuators with latching mechanisms. The artificial muscle actuators may also be electrically activated to displace the displacement device into or out of one or more of these stable positions.

The latching mechanisms may be utilized fully with either linear or rotational artificial muscle actuators and may be combined with the use of bi-stable artificial muscle actuators if desired. A bi-stable artificial muscle actuator is one which may not require a continuous supply of energy to remain actuated. A bi-stable artificial muscle actuator can maintain its position without the need for external latches, gears, magnets or the constant application of current to produce heat. Bi-stable artificial muscle actuators may be used in combination with the latches, gears and magnets, to produce a more robust design.

In one or more embodiments, a linear displacement device providing linear displacement comprises a rotational artificial muscle actuator. A rotational artificial muscle actuator, also referred to as a torsional artificial muscle actuator, is one that twists (or untwists) upon actuation. These rotational artificial muscle actuators may have an attached piece, or arm, that converts the rotational motion of the artificial muscle actuators into linear motion for a body.

Among the advantages of the linear displacement device are the low cost of materials, a simple design, and the ability to replace springs with a device that allows for control and does not require the device to return to a specific position when not activated. In addition, the linear displacement device may be actively or passively thermally controlled. An example of passive thermal control may be actuation based on ambient temperature. Active control may include activation of the artificial muscle actuator using electrical current. Further, the materials comprising the linear displacement device may be selected to provide necessary resistance to heat, corrosion, and the like.

Figure 3:
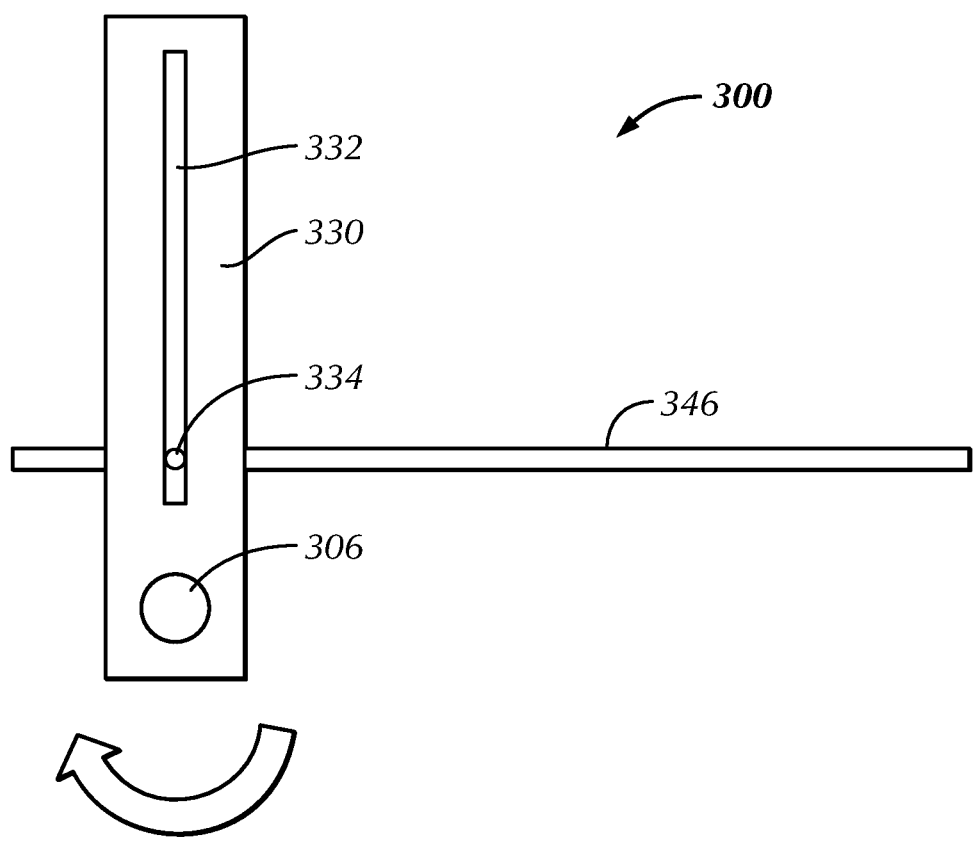
FIG. 3 is a schematic of a linear displacement device comprising a rotational artificial muscle actuator in accordance with one or more embodiments disclosed herein.

As shown in FIG. 3, in one or more embodiments, the linear displacement device 300 may comprise at least one artificial muscle actuator 306 (shown in end view) designed to rotate with application of heat. The heat may be provided by passive or active thermal control. Passive thermal control may be a direct response to the ambient temperature. In one or more embodiments, active thermal control is provided through electrical current passing through a wire (not shown) wound around the artificial muscle fiber. Attached to the artificial muscle actuator is a means to convert the rotational motion of the muscle actuator into the linear motion of the linear displacement device. The means may include a gear system attached to the artificial muscle actuator 306. This may comprise a simple arm 330 attached to the artificial muscle actuator. In one or more embodiments, the arm 330 may be a straight piece. The arm 330 may be attached at or near the midpoint of the length of the artificial muscle actuator 306. When the artificial muscle actuator 306 is rotated, the arm 330 rotates with it. In other words, the arm 330 rotates in concert with the rotational artificial muscle actuator 306. A body 334 may be positioned on the surface of the arm 330.

In one or more embodiments, the arm 330 includes a channel 332 in which body 334 may be constrained to move. Further, a stationary channel 346 may also be provided to constrain, or restrict, the motion of body 334 to be linear along the direction of stationary channel 346. In one or more embodiments, stationary channel 346 may be simply another surface while another force, for example gravity, provides a constraint to keep body 334 in contact with stationary channel 346.

When the rotational artificial muscle actuator 306 is rotated the arm 330 will exert a rotational force on the body 334. Either the connection between the body 334 and the arm 330 or the body 334 itself should be configured so that the body 334 may be displaced only in a linear direction.

In one or more embodiments, a rack and pinion system may be used to translate rotational motion into linear displacement.

In one or more embodiments, the linear displacement device 300 comprises two artificial muscle actuators, each having an arm operating so that both artificial muscle actuators produce linear displacement simultaneously. In one or more embodiments, the linear displacement device may comprise more than two artificial muscle actuators.

The linear displacement device may further be configured to have a latching mechanism to firmly maintain the linear displacement device in a particular position. Latching mechanisms may be mechanical, magnetic, or any other suitable method for fixing the position of the linear displacement device.

In one or more embodiments, the arms may be designed to open and close valves, in a gate fashion. In one or more embodiments, the arm described above may comprise a paddle. Two or more artificial muscle actuators with said paddles attached may then be configured so that their paddles meet precisely, sealing a valve. With the application of heat, either passively or actively, the artificial muscle actuators may rotate and open the valves. The valves may be configured to open in the same direction, or they may each open in opposite directions. They may also be configured to operate independently of each other. Furthermore, the artificial muscle actuators with paddles attached may be laid out end to end, so a large span may be controlled by many of these artificial muscle actuators. This approach may provide for better control over fluid flow in a pipe, tube, or similar object, with many small apertures opening rather than a few large apertures. This arrangement of artificial muscle actuators with paddles may prevent non-uniform fluid flow.

Figure 4:
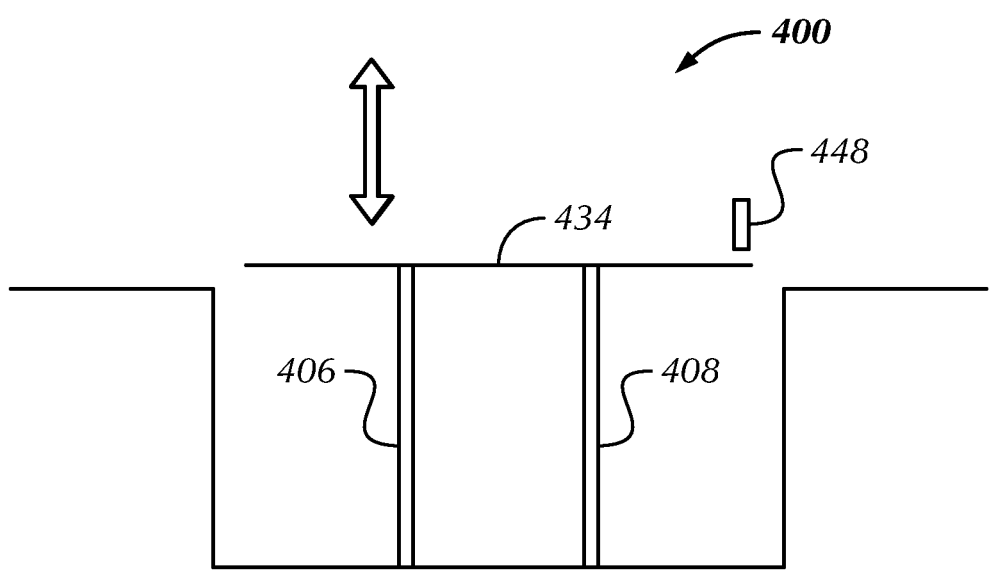
FIG. 4 is a schematic of a linear displacement device comprising a linear artificial muscle actuator in accordance with one or more embodiments disclosed herein.

As shown in FIG. 4, in one or more embodiments, linear actuating muscle actuators 406, 408 may be used in a linear displacement device 400. In one or more embodiments using linear actuating muscle actuators, one homochiral 406 and one heterochiral 408 muscle actuator may be placed directly beside each other. A homochiral muscle actuator 406 is one that contracts linearly when heated, the direction of twist being the same as the direction of coiling. In contrast, a heterochiral muscle actuator 408 expands linearly when heated; the direction of twist being the opposite from the direction of coiling.

The linear displacement device 400 may be used to expose a body 434 from an otherwise flush surface. Similarly, the linear displacement device 400 may be used to hide a body 434 that extends from a flush surface. Upon the application of force the body 434 will return to its position like a spring, yet can still be controlled as if connected to a motor. In one or more embodiments, a linear displacement device may be used as a camera lens extender, a Braille e-reader, texture control (e.g., an array of pins), changing surface roughness, and automatic suction cups.

To move this linear displacement device 400 from the down position into the up position, the heterochiral muscle actuator 408 is activated causing the muscle actuator 408 to expand, pushing the linear displacement device 400 to the extended position. In one or more embodiments, a latching mechanism 448 is used to maintain the position of the linear displacement device 400 in the extended state. In order to retract the linear displacement device 400 into its retracted state the homochiral muscle actuator 406 is activated, which contracts and pulls the linear displacement device 400 into its retracted state.

In one or more embodiments, the homochiral muscle actuator 406 may be replaced by any actuator which retracts lengthwise. The heterochiral muscle actuator 408 may also be replaced by any actuator which extends lengthwise.

Figure 5A:
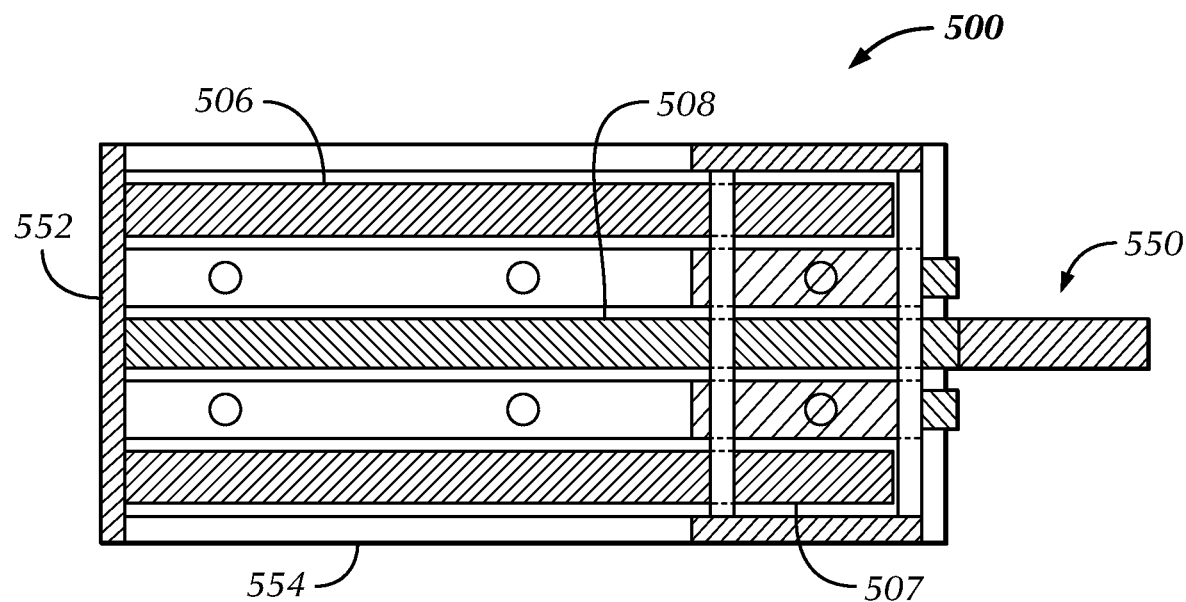
FIG. 5 is a schematic of a linear displacement device as a piston modules comprising linear artificial muscle actuators in accordance with one or more embodiments disclosed herein.
Figure 5B:
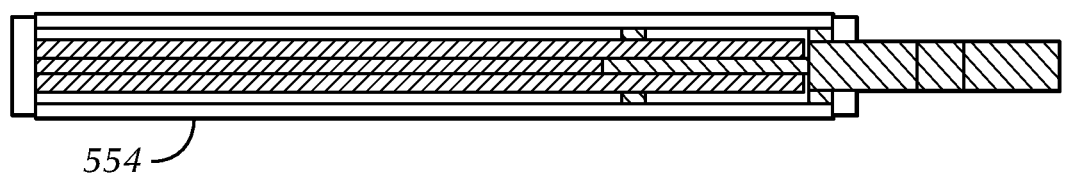

As shown in FIG. 5, in one or more embodiments, a linear displacement device may be used as a piston module 500. The module 500 may comprise a piston 550 in a housing 554. The housing face opposite the piston 550 may comprise a copper ground 552 for artificial muscle actuators 506, 507, and 508. Artificial muscle actuators 506, 507, 508 may attach at one end to the housing at the copper ground and to the piston at the other end. In one or more embodiments, the piston module 500 comprises at least one puller artificial muscle actuator 506, 507. The puller artificial muscle actuator 506, 507 may be used to pull piston 550 toward the copper ground 552. The puller artificial muscle actuator 506, 507 may be a homochiral muscle actuator. The piston module 500 may also comprise a pusher artificial muscle actuator 508. The pusher artificial muscle actuator 508 may be used to push the piston 550 away from the copper ground 552. The pusher artificial muscle actuator 508 may be a heterochiral muscle actuator. The artificial muscle actuators 506, 507, 508 may be actuated individually or in various combinations. Actuation may be by electrical current or by other actuation means as disclosed herein. In one or more embodiments, piston module 500 may comprise a high-temperature material for non-actuator and non-metallic parts. This material may be, for example, Teflon.

Figure 6:
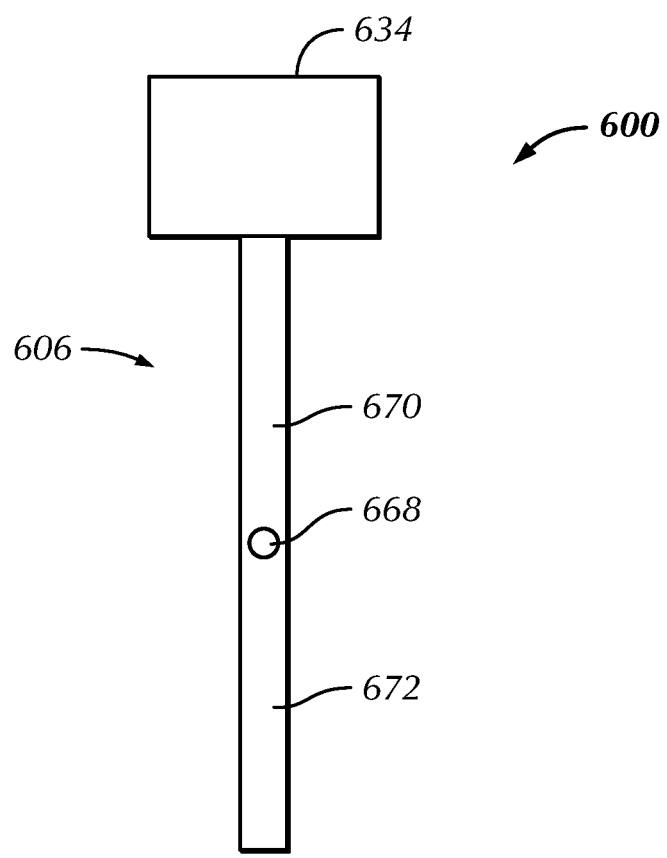
FIG. 6 is a schematic of a linear displacement device in accordance with one or more embodiments disclosed herein.

As shown in FIG. 6, in one or more embodiments, a single linear actuating muscle actuator may be used in a linear displacement device 600. A pin 668 may be secured into the center of the artificial muscle actuator 606. The actuating muscle actuator 606 may be considered divided into two segments by the pin 668. One end of the first segment 670 may be attached to the center pin. The other end of the first segment may be attached to the body 634 that one desires to displace. The first segment 670 may be activated by passing electric current through it. The electric current may cause the artificial muscle actuator 606 to expand, lifting the body 634 into its extended state. A side effect is that the second segment 672 will up-twist and contract. Up-twist means that the fiber in the coiled segment being compressed is receiving twist from the coil. Up-twist may be the result of compressing a homochiral coil. Once the body 634 has reached its desired extended position, then it may be held there by latches or other latching mechanisms 648.

To retract the body 634 into its retracted state the second artificial muscle actuator segment 672 is activated causing it to extend and up-twist the first segment 670. The up-twisting causes the first segment 670 to contract forcing the body 634 into the retracted position.

The linear displacement device may be made to operate in many ways. The artificial muscle actuators, in any configuration, may be used to place the linear displacement device in the extended position. An electric current may be used to heat and actuate the muscle actuators causing linear motion of the body. The device may then have a series of latches or magnets which hold the device in the extended position without requiring that the artificial muscle actuators be continuously heated. Upon the application of sufficient external force, the latching mechanism may be overcome and the linear displacement device may be positioned in its retracted position. If desirable the device may be maintained in its retracted position using a latching mechanism or through muscle actuation. Alternatively, the linear displacement device may be configured to return the device to its extended position through muscle actuation.

In one or more embodiments, the artificial muscle actuator may be operated bi-stable mode so that it automatically returns to the extended position. In this case the latching mechanism on the extended position can be used to simply prevent small oscillations in the muscle actuator and to provide a threshold amount of force necessary to cause the linear displacement device to displace. In this way the artificial muscle actuator may passively act as a spring, returning the linear displacement device to its original state and can be actively actuated.

In one or more embodiments, the artificial muscle actuators may be designed to operate as bi-stable polymer actuators. This would enable the artificial muscle actuators to maintain their position without the need for external latches, gears, magnets or the constant application of current to produce heat. In one or more embodiments, the bi-stable artificial muscle actuators may be used in combination with the latches, gears, and magnets, to produce a more robust design.

Figure 7:
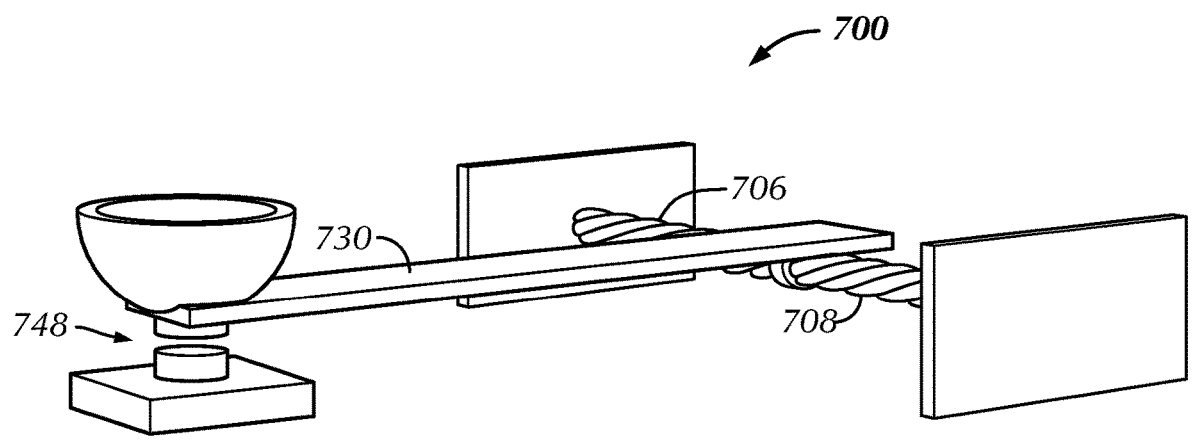
FIG. 7 is a schematic of a mechanical accumulator, or catapult, in accordance with one or more embodiments disclosed herein.

As shown in FIG. 7, one or more embodiments of the invention are directed to a mechanical accumulator 700, or catapult, that utilizes an artificial muscle actuator 706. In one or more embodiments, the artificial muscle actuator 706 may comprise a plurality of artificial muscle actuators 706, 708.

In these embodiments, an artificial muscle actuator 706, 708 may be used in conjunction with a latching mechanism 748. The latching mechanism 748 is designed to prevent the artificial muscle actuator 706, 708 from causing movement when the artificial muscle actuator is first activated. Possible latching mechanisms include magnets, mechanical latches, and other artificial muscle actuators among others. Any means to hold the muscle actuators at a particular position, until the muscle actuator can generate sufficient force to break free of the latching mechanism may be used. Another artificial muscle actuator can be used as latching mechanism 748 to hold the position of artificial muscle actuator 706, 708 while torque is generated in accordance with embodiments disclosed herein. The latching mechanism artificial muscle actuator may be caused to release allowing the torque generating artificial muscle actuator 706, 708 to overcome it and rapidly actuate.

An advantage of using an artificial muscle actuator as a latching mechanism is it allows for user control over the exact tension required to actuate to be done by using software at the local level. Thus, the predetermined amount of force required to overcome the latching mechanism artificial muscle actuator may be varied by a user. A single product may be produced with the user programming the linear displacement device to release at specific tension. An actuating means causes the artificial muscle actuator, or fiber, to initially accumulate energy. When the accumulated energy is sufficient to overcome the latching mechanism 748, the latching mechanism suddenly releases resulting in a forceful actuation. In one or more embodiments, a bundle of artificial muscle fibers may be used because of the increased torque produced by a bundle of artificial muscle fibers in comparison to a single artificial muscle actuator of comparable dimensions. However, embodiments disclosed herein are not limited as such.

Examples of the actuating means include, but are not limited to, a heater, or electrically applying heat to the artificial muscle fibers. Examples of the latching mechanism 748 include, but are not limited to, magnets, mechanical latches, other artificial muscle actuators, or combinations thereof.

Any means to hold the artificial muscle fibers in a particular position, until the muscle actuator can generate sufficient force to break free of the latching mechanism may be used. For example, another artificial muscle actuator may be used to hold the position of another actuator while it generates torque. In these embodiments, the holding artificial muscle actuator may be actuated to release.

In one or more embodiments of the mechanical accumulator 700, the mechanical accumulator may include multiple latching mechanisms to grant a multitude of stable positions. For example, an artificial muscle actuator may have two stable positions to function as a valve designed to be either completely closed or completely open. In such embodiments, the artificial muscle actuator may be initially activated to generate torque and, when the latching mechanism is deactivated, the artificial muscle actuator will release and quickly transfer into another stable position. The rapid application of force in these embodiments may be beneficial to overcoming any resistance in such a valve, for example by a fluid flowing through the valve. The rapid application of force may also prevent the valve from being in an intermediate state between open and closed.

Electrical current is used to heat the artificial muscle actuator, either an individual fiber or a plurality of fibers in a bundle, which is held steady by a latching mechanism. While the muscle actuators are being heated, they generate internal stresses which would normally be relieved by the rotational motion of the artificial muscle actuators, but the latching mechanism prevents rotation, forcing the energy to accumulate within the muscle actuator. When the internal tension is sufficiently strong, it will overcome the resistance of the latching mechanism and the muscle actuator will actuate rapidly and forcefully.

As always with artificial muscle actuators, they may be actively powered using electrical current or they may be passively powered from environmental temperature conditions.

Further, without having the benefit of a latching mechanism to accumulate tension, a similar rapid actuation may be achieved. A large current applied very quickly to a thick artificial muscle actuator may to generate rapid actuation. Such large currents applied so quickly require a capacitor and conductors which can withstand said large currents. Both the capacitor and the more durable conductor, for example a thicker gauge wire, may increase manufacturing complexity and cost.

The mechanical accumulator may effectively diminish the need for large currents applied quickly and prevent the commensurate strain on supporting electrical systems and the artificial muscle actuator itself.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A linear displacement device comprising:
   a first artificial muscle actuator and a second artificial muscle actuator; and
   a body that is restricted to move linearly, the body having a first surface and a second surface that opposes the first surface;
   wherein the first artificial muscle actuator and the second artificial muscle actuator are configured to cause the body to move linearly,
   the first artificial muscle actuator expanding when actuated, thereby causing the body to move in a linear direction away from a base,
   the second artificial muscle actuator contracting when actuated, thereby causing the body to move in the linear direction towards the base,
   wherein a first end of each of the first artificial muscle actuator and the second artificial muscle actuator is attached to a same surface of the base, and a second end of each of the first artificial muscle actuator and the second artificial muscle actuator is attached to the second surface of the body, and
   wherein both the first artificial muscle actuator and the second artificial muscle actuator extend between the same surface of the base and the second surface of the body.

2. The linear displacement device of claim 1, further comprising:
   a latch provided facing the first surface of the body and holding the linear displacement device in a first position, wherein the linear displacement device is configured to move towards a second position when an external force is applied to at least one of the first artificial muscle actuator and the second artificial muscle actuator.

3. The linear displacement device of claim 1, wherein:
the first muscle actuator is a heterochiral artificial muscle actuator, and
the second muscle actuator is a homochiral artificial muscle actuator.

* * * * *